April 9, 1963 TAKEO YUGE ETAL Plant Pat. 2,247

AZALEA PLANT

Filed Feb. 20, 1961

INVENTORS
TAKEO YUGE
KANJI K. YUGE
BY Spensley and Horn
ATTORNEYS

United States Patent Office

Plant Pat. 2,247
Patented Apr. 9, 1963

2,247
AZALEA PLANT

Takeo Yuge and Kanji K. Yuge, both of
177 E. Mariposa St., Altadena, Calif.
Filed Feb. 20, 1961, Ser. No. 90,609
1 Claim. (Cl. 47—60)

This invention relates to a new and distinct variety of azalea plant characterized particularly by its early and extended blooming season and its deep rose-pink flowers which are produced profusely on a plant of fine, uniformly compact growth habit. The present variety commences blooming in September and is heavily in bloom in December in southern California without forcing or heating. Blooming continues through January with flowers that are long lasting with no fading or color change as the flowers age. Each of the flowers will last at least three weeks with each bud blossoming into two to three separate flowers. The plant has very showy buds with the flower stem being about one-half inch long carrying straight upright buds.

This variety of azalea plant was produced in the experimental garden of the applicants' nursery at Altadena, California; the variety being the result of a cross between a Belgian semi-double unpatented variety known as Miss Cottage Gardens and a Belgian Indica azalea being a selected double seedling of the inventors known as Kaho, a variety which is unpatented. This cross pollination was carried out in the applicants' nursery at Altadena, California in February 1950, the seeds resulting from the cross pollination were collected in November 1950 and planted in March 1951. The seedlings produced in this manner were observed over an extended period of time and this particular variety was selected and segregated.

Upon the cross being recognized as novel, and particularly when the extended and early blooming season of the variety was found, it was taken for propagation by cuttings at the aforesaid nursery in Altadena, California and such cuttings produced azalea plants which carried forward all of the new and distinct features of the subject original plant. Subsequent propagation of the variety by cuttings further evidenced that the variety is fixed in its floricultural characteristics.

In the accompanying illustration:

Figure 1:
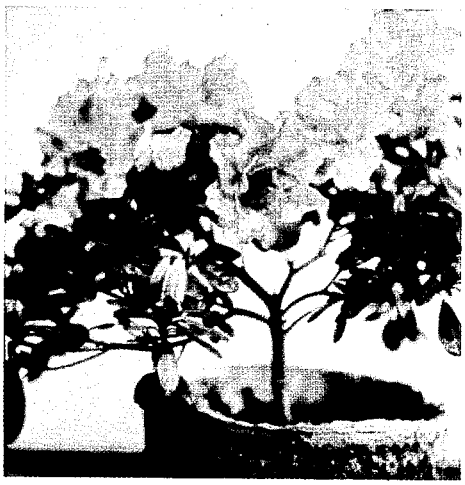
FIGURE 1 is a perspective view showing the flowers in bloom.
Figure 2:
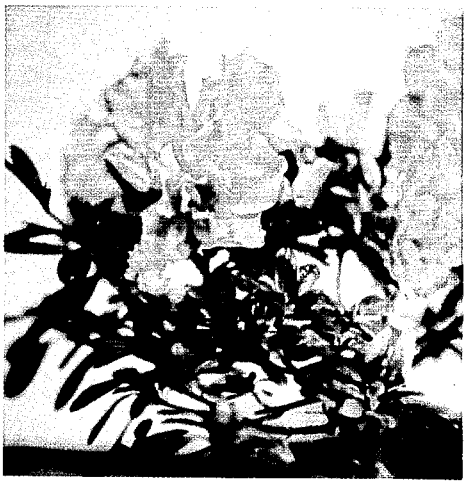
FIGURE 2 is a perspective view of a stem, with leaves and flowers.
Figure 3:
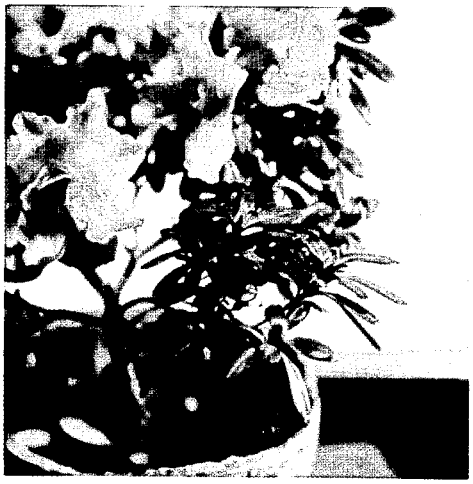

Referring now more specifically to the botanical details of the new and distinct variety of azalea plant of the present invention, the following is an outline description of the same:

*Plant*

Form: Many branched, rounded, symmetrical form.

Growing habit: Dense and bushy with heavy glossy green foliage. The rate of growth is rapid and more rapid than most Belgian varieties.

Blooming habit: Flowers bloom out evenly over the entire plant when forced in the greenhouse or flowered naturally in the garden. Usually two to three separate flowers blossom from each bud produced on each stem. Showy buds with flower stem about ½ inch long carrying straight, upright buds.

Blooming season: September through January in southern California without forcing or heating. The plant is heavily in bloom in southern California in December.

Foliage: Glossy.

*Size.*—Mature foliage 1½" to 2" long and ⅝" to ¾" in width.

*Color.*—Top—dark green; bottom—light green. (See chart below.)

*Shape.*—Obovate. Elliptic; slightly mucronate tip.

*Aspect.*—Glossy with some hairs on both sides. (Slightly pubescent on both sides.)

*Texture.*—Medium.

*Edges.*—Entire—not serrated.

*Ribs and veins.*—Pinnately veined. Five veins leading off main center vein, multiple small veins leading off the five veins.

*Flower*

Size: Average 3½" to 4" in diameter by 2" in length.

Borne: Two or three each stem.

Stem: Medium length with sufficient strength to hold the flowers properly.

Form: Semi-fringed double.

Permanence: Long lasting without fading or changing color as flowers age. Flowers last average of at least three weeks in southern california.

Petalage: Six outer petals, ten inner petals in three layers.

Color: Deep rose pink. (See chart below.)

Petals:

*Texture.*—Medium to heavy.

*Appearance.*—Velvety with edges ruffled.

*Shape.*—Elongated, wavy, obovate.

*Arrangement.*—Inner petals in three layers. The lower part of each petal is grown together with the lower part of an adjacent petal in the next layer.

*Persistence.*—Remains firm without wilting or color change until flower falls.

Reproductive organs:

*Style.*—Well developed.

*Ovaries.*—Normal.

The color designations according to "A Dictionary of Color" by Maerz and Paul are as follows:

| Part | Color | Plate | Letter | Number |
|---|---|---|---|---|
| Foliage: | | | | |
| New Leaves | Spinach Green | 22 | K | 7 |
| Mature Leaves | Wintergreen English Ivy. | 23 | A | 12 |
| Stems (New Growth) | Chutney | 7 | J | 12 |
| Flower: | | | | |
| Outer Edge of Petals | Bridal Rose | 3 | F | 6 |
| Base of Petals | | 3 | J | 4 |

Having thus disclosed our invention, we claim:

The new and distinct variety of azalea plant substantially as herein shown and described being a cross between a Belgian semi-double variety known as Miss Cottage Gardens and a Belgian double, Kaho, and characterized by its early and extended blooming season.

No references cited.